United States Patent [19]

Suzuki et al.

[11] Patent Number: 4,715,369

[45] Date of Patent: Dec. 29, 1987

[54] METHOD OF TREATING AN INJURED PART ON THE ORAL MUCOSA AND THE COVERING MATERIAL FOR USE THEREOF

[75] Inventors: Yoshiki Suzuki; Hiroshi Ikura, both of Hino; Gentaro Yamashita, Tachikawa; Tsuneji Nagai, Taito, all of Japan

[73] Assignee: Teijin Limited, Osaka, Japan

[21] Appl. No.: 13,175

[22] Filed: Feb. 9, 1987

Related U.S. Application Data

[63] Continuation of Ser. No. 741,064, Jun. 25, 1985, abandoned, which is a continuation of Ser. No. 594,951, Apr. 2, 1984, abandoned, which is a continuation of Ser. No. 335,418, Dec. 29, 1981, abandoned.

[30] Foreign Application Priority Data

Dec. 29, 1980 [JP] Japan .................. 55-185294

[51] Int. Cl.$^4$ .................. A61L 15/01; A61K 9/24
[52] U.S. Cl. .................. 128/156; 424/435; 523/111
[58] Field of Search .................. 523/111; 128/156; 424/435, 434; 604/307

[56] References Cited

U.S. PATENT DOCUMENTS 4,250,163  2/1981  Nagai et al. .................. 424/14
4,292,299  9/1981  Suzuki et al. .................. 424/16

Primary Examiner—Paul Lieberman
Assistant Examiner—Linda D. Skaling
Attorney, Agent, or Firm—Sughrue, Mion, Zinn, Macpeak & Seas

[57] ABSTRACT

The present invention relates to a method for treating an injured part on the oral mucosa, which comprises covering the injured part with a covering material consisting essentially of a cellulose lower alkyl ether and a polyacrylic acid or its pharmaceutically acceptable salt, and to said covering material.

According to the present invention, without using a medicament, the injured part on an oral mucosa can be cured rather rapidly simply by covering the injured part.

3 Claims, No Drawings

METHOD OF TREATING AN INJURED PART ON THE ORAL MUCOSA AND THE COVERING MATERIAL FOR USE THEREOF

This is a continuation of application Ser. No. 741,064, filed June 25, 1985, now abandoned, which is a continuation of application Ser. No. 594,951, filed Apr. 2, 1984, now abandoned, which is a continuation of Ser. No. 335,418, filed Dec. 29, 1981, now abandoned.

BACKGROUND OF THE INVENTION

1. Field of the Invention

The present invention relates to a method for treating an injured part on the oral mucosa, which comprises covering the injured part with a covering materials to be used for protecting the injured part from extrinsic irritations, and to said covering material.

More particularly, this invention relates to a method for treating an injured part on the oral mucosa, which comprises covering the injured part with a covering material which is characterised by covering the injured oral mucosa suffering from aphtha, wound, erosion, canker, etc. to protect the injured part from extrinsic irritations caused by the tongue, tooth, food, etc. for many hours by adhering to the injured part on the oral mucosa while it gradually becomes swollen and soft upon absorbing saliva or secretion, and to said covering material.

2. Description of the Prior Art

In the past, almost nothing has been known as a covering material to protect an oral mucosa injury such as aphtha, etc. from extrinsic irritations, except for some ointment bases such as petrolatum, etc. applied to such purpose. However, such ointment bases as petrolatum, etc. are unsatisfactory as a covering material to protect the injured part on the oral mucosa from extrinsic irritations in view of the fact that, having no adhesion to the injured mucous membrane, they would come off or run down and that they make the patient unpleasant by filling the mouth with unctuous materials.

Japanese Laid-Open Patent Publication No. 38412/76 discloses a buccal preparation composed of a medicament, an excipient (i.e., crystalline cellulose, mannitol, lactose, surbitol, anhydrous calcium phosphate, amylose), and a sodium salt of polyacrylate having a property to adhere to a diseased part in the oral cavity and also a property to swell; however, a study conducted by the present inventors points to a conclusion that the preparation consisting of a sodium salt of polyacrylate, excipient, and medicament does not always serve satisfactorily as a covering material for the injured oral mucosa, since it often fails to show enough adhesion, swells too much taking an irregular shape and makes the patient feel uncomfortable, tastes bad, stimulates the secretion of saliva, and is apt to drop off or run down.

On the other hand, Japanese Laid-Open Patent Publication No. 41320/79 discloses a show-releasing medical preparation to be administered by adhering to the oral mucosa comprising hydroxypropyl cellulose, polyacrylic acid or its pharmaceutically acceptable salt, and a medicament. Japanese Laid-Open Patent Publication No. 62012/80 discloses a slow-releasing medical preparation to be administered by adhering to a wet mucosa surface comprising an adhesive layer composed of a polymer which has the adhesiveness to a wet mucosa surface (i.e., hydroxypropyl cellulose, polyacrylic acid or its pharmaceutically acceptable salt) and a nonadhesive layer composed of lactose, starch, etc. and at least either one of said adhesive layer and nonadhesive layer is made to contain a medicament.

However, in the two Japanese patent document cited above, it is not at all disclosed and suggested that the preparation consisting essentially of a cellulose lower alkyl ether and a polyacrylic acid or its pharmaceutically acceptable salt and not containing a medicament can be used to cover the injured part on the oral mucosa and has an ability enough to cure the injured part suffering from aphtha, wound, erosion, etc.

SUMMARY OF THE INVENTION

We have found as a result of the earnest research work that, in case where an oral mucous membrane is injured, the injured part can be cured rather rapidly simply by covering the injured part for protection because of natural self-healing powers inherent in a living body and that the preparation consisting essentially of a cellulose lower alkyl ether and a polyacrylic acid or its pharmacentically acceptable salt is most suitable for covering material.

The present invention relates to a method for treating an injured part on the oral mucosa, which comprises covering the injured part with a covering material consisting essentially of a cellulose lower alkyl ether and a polyacrylic acid or its pharmaceutically acceptable salt, and to said covering material.

The following points may be mentioned as leading characteristics of the method and covering material offered by the present invention:

(1) Without using a medicament, the injured part on an oral mucosa can be cured rather rapidly simply by covering the injured part for protection.

(2) The covering material adheres to the injured part upon absorbing saliva or secretion and has an excellent adhesiveness to the injured part even after it is swollen with moisture.

(3) Though it gradually becomes swollen and soft by absorbing saliva or secretion, it remains insoluble not to run down and has an outstanding covering effect on the injured part without breaking loose remarkably even in a swollen state.

(4) It keeps on covering the injured part for a long time after becoming swollen and soft.

(5) The preparation, which is swollen and soft, not only scarcely irritates the injured part but also protect the injured part by intercepting the extrinsic physical and chemical irritation caused by the tongue, tooth, and food.

(6) The adhesion to the injured part and effective covering time can be adjusted by changing the quantitative ratio of cellulose lower alkyl ether to polyacrilic aid or its pharmaceutically acceptable salt.

DESCRIPTION OF THE PREFERRED EMBODIMENTS

A covering material offered by the present invention is necessarily to contain both cellulose lower alkyl ether and polyacrylic acid or its pharmaceutically acceptable salt and only such combined use of constituents makes a covering material which has the aforementioned characteristics.

Cellulose lower alkyl ether and polyacrylic acid or its pharmaceutically acceptable salt are respectively water-soluble polymers. Therefore, when each of them is used individually, both are not proper for making a covering material to be used by adhering to the injured oral mucosa since such covering material breaks down or dissolves to run down in the presence of secretion. However, the covering material containing the two constituents possesses the desirable quantity of swelling, but not dissolving and running down, and maintains its excellent adhesion to an affected part even in the swollen state and retains its form as well and continues to cover the injured part effectively for a long time.

Cellulose lower alkyl ether used in the present invention is one with several of its hydroxyl groups of cellulose are at least partially substituted by the same or different lower alkyl ether groups. A lower alkyl group of the lower alkyl ether group may be substituted by a substituent group. As said substituent group, a hydroxyl group or alkali metal carboxylate group such as sodium carboxylate group may be mentioned as a desirable one. As lower alkyl group which may be substituted, there are a methyl group, hydroxy lower alkyl groups having 2 to 3 carbon atoms, and carboxylate groups formed between metals and carboxy lower alkyl groups having 2 or 3 carbon atoms.

As lower alkyl group which may be substituted as mentioned in the above, methyl, ethyl, n-propyl, iso-propyl: or β-hydroxyethyl and β-hydroxypropyl; or carboxymethyl, α-carboxyethyl, and β-carboxyethyl forming carboxylates with alkali metal may be mentioned.

As cellulose lower alkyl ether, methyl cellulose, hydroxyethyl cellulose, hydroxypropyl cellulose, hydroxypropylmethyl cellulose, carboxymethylhydroxyethyl cellulose sodium carboxymethyl cellulose, etc. may be mentioned.

Of those mentioned above, methyl cellulose, hydroxypropyl cellulose and hydroxypropylmethyl cellulose are preferably used, and hydroxypropyl cellulose is especially preferable from a viewpoint of the effect of covering the injured part on the oral mucosa.

In the present invention, only one of these cellulose lower alkyl ethers or a mixture of two or more of them can be used.

Also in the present invention, cellulose lower alkyl ethers of any molecular weight can be used; however, as a constituent of a covering material of the present invention having desirable characteristics as mentioned above, it is preferable to use those which have the viscosity of 3 to 10,000 centipoises in a 2% by weight aqueous solution at 20° C., more preferably 1,000 to 4,000 centipoises.

Also, polyacrylic acid or its pharmaceutically acceptable salt of any molecular weight can likewise be used; however, it is preferable to use those which have the viscosity of 360 to 165,000 centipoises, more preferably in the range of 3,600 to 16,500 centipoises, when measured at 25.0±0.5° C. in an aqueous solution of its sodium salt at pH from 7 to 7.5 having the concentration of 0.2% by weight as polyacrylic acid.

As for the polyacrylic acid referred to in the present invention, the use of a simple substance of polyacrylic acid is perfectly right and those available on the market containing other water-soluble polymer, etc. (generally 20% by weight or less) can also be used.

What is referred to as polyacrylic acid in the present invention includes not only a polyacrylic acid homopolymer but also a copolymer of acrylic acid and metaacrylic acid, ether monomer of vinyl type, etc., in which case the mixing ratio of the copolymerization should naturally be limited to such a ratio as to make the present invention achieve its objective.

Also what is referred to as a pharmaceutically acceptable salt of polyacrylic acid should be construed as salts of the abovementioned polyacrylic acids.

The ratio between cellulose lower alkyl ether and polyacrylic acid or its pharmaceutically acceptable salt to be contained in the preparation differs depending upon the molecular weight of the respective constituents and the selected use of either polyacrylic acid or its salt; however, when based on the weight of cellulose lower alkyl ether, it is generally advisable to use 0.1 to 10 parts by weight of polyacrylic acid or its pharmaceutically acceptable salt against 10 parts by weight of cellulose lower alkyl ether. More particularly, it is advisable to use 0.1 to 3.0 parts by weight of polyacrylic acid against 10 parts by weight of cellulose lower alkyl ether and 0.5 to 3.0 parts by weight of pharmaceutically acceptable salt of polyacrylic acid against 10 parts by weight of cellulose lower alkyl ether respectively.

The difference in range of desirable amount between polyacrylic acid and its pharmaceutically acceptable salt is due to the fact that pharmaceutically acceptable salt is somewhat inferior in strength to polyacrylic acid when the preparation is in the swollen state.

As pharmaceutically acceptable salt of polyacrylic acid, it is desirable to use its alkali metal salt such as sodium salt, potassium salt, etc. or ammonium salt and no limit is fixed as to the degree of neutralization.

A covering material used by adhering to the injured part on the oral mucosa according to the present invention is prepared by making a thoroughly mixed and homogeneous mixture of cellulose lower alkyl ether, polyacrylic acid or its pharmaceutically acceptable salt, and, as occasion demands, one or more than one kinds of lubricant, binder, excipient, coloring agent, and corrigent which are used to improve the apperance, taste and smell, and by granulating after once making the mixture into a slug, or by pressure-forming a proper amount of such slug or granule into a desired shape with the use of a punch, die, or press.

Here, the homogeneous mixture should be interpreted as having the respective constituents contained in the preparation uniformly intermixed, not allowing any portion of the respective constituents to be distributed locally.

It is generally convenient to mix the respective constituents prepared in a state of fine powder. Besides tables, the preparation may be made into any shape appropriate to the condition of the diseased part. For instance, such shape of the preparation as granule, and dental cone may be mentioned. A granular preparation can be made by granulizing the pressure-formed slug.

Lubricants to be used according to the need include tale, stearic acid and its salt, wax, etc.; binders include starch, dextrin, tragranth, gelatin, polyvinyl pyrrolidone, lyndroxy propyl cellulose, polyvinyl alcohol, etc.; excipients include starch, crystalline cellulose, dextrin, lactose, mannitol, sorbitol, calcium phosphate anhydride, etc.; and corrigents include citric acid, fumaric acid, tartaric acid, menthol, citrus scent, etc.

In addition to the abovementioned excellent efficacy attributed to the preparation of the present invention, its merrits are that it covers the injured part on the oral mucosa while rataining the swollen state for a comparatively long time without dissolving or running down, that it gives no feeling of touchy discomfort to the patient, alleviating an urge to crush the drug with the teeth or tear off the preparation with the tongue, that it causes no difficulty in daily life including speaking, eating, drinking, sleeping, etc., and that it can be removed easily at any time if necessary, thus much facilitating the medical care.

On the other hand, the main cause which leads to the delaying of the recovery of an oral mucosa injury is that the oral cavity is an organ which takes in and musticates food and also is an organ to vocalize. It is assumed that the delayed recovery of the injured oral mucosa is due to the extremely weakened natural self-healing powers inherent in a living body resulting from a variety of extrinsic irritations to which the injured oral mucosa is exposed, including acid or salty irritants contained in the food, contact with a solid material, tooth, tongue, etc., and contortion of the injured mucosa arising from phonation. A covering material of the present invention swells and forms a covering when administered to the effected part to prevent the infiltration of acid and salt into the injured part and interrupt direct contact between a solid material, tooth, tongue, etc. and the injured part, and, furthermore, it is deformable and is scarcely irritant itself. Therefore, it may be concluded that it can cover and protect the injured part for a considerably long time to actively promote natural self-healing powers inherent in a living body, thus allowing the injured part to recover from a diseased condition much earlier.

The preparation of the present invention is an excellent preparation as is mentioned above; however, it will become a more preferable one which can be more easily administered in the oral cavity with accuracy and can also be applied even to the fexure, when it is prepared in a two-layer tablet comprising a covering material, which consists of cellulose lower alkyl ether and polyacrylic acid or its pharmaceutically acceptable salt, and a nonadhesive layer which has no adhesion to the wet oral mucosa. Therefore, the present invention also provides a method for treating an injured part on the oral mucosa, which comprises covering the injured part with a covering material consisting of a adhesive layer consisting essentially of cellulose lower alkyl ether and polyacrylic acid or its pharmaceutical acceptable salt and a nonadhesive layer having no adhesion to the wet oral mucosa, and said covering material.

An awkwardness experienced with the administration of the preparation by involuntary adhesion of the preparation to an undesired part can be eliminated by use of a two-layer tablet having a nonadhesive layer. The preparation thus consisting of two layers has another merit of making the thickness of the adhesive layer thinner because the nonadhesive layer and the adhesive layer comprising cellulose lower alkyl ether and polyacrylic acid or its pharmaceutically acceptable salt mutually reinforce each other. The thin preparation alleviates the feeling of touchy discomfort and further makes itself applicable to the flexure even along its bent part.

Cellulose lower alkyl ether and polyacrylic acid or its pharmaceutical acceptable salt used in preparing the abovementioned two-layer tablet are the same ones as used in preparing the aforementioned covering material, and the preparation is made in the same way and in the same making up ratio.

As for the constituents which make up the nonadhesive layer, it is recommendable to use water-soluble or water-disintegrable substances, since they alleviate the feeling of touchy discomfort.

As the constituents to make up such nonadhesive layer, lactose, glucose, sucrose, starch, crystalline cellulose, carboxymethyl cellulose calcium, dextrin, cyclodextrin, silicic acid anhydride, aluminum silicate, talc, calcium stearate, magnesium stearate, bees wax, polyethylene glycol, polyphosphate, anhydrous calcium phosphate, hydroxypropyl cellulose etc. may be mentioned. One or more than one of these substances may be used as constituents to form the nonadhesive layer and the nonadhesive layer may also contain the aforementioned other ingredients such as known excipient, binder, disintegrator, coloring agent, corrigent, and lubricent.

The preparation of the present invention has the aforementioned excellent characteristics and can be prepared according to the following process, for instance.

It can be prepared conveniently by first making a homogeneous mixture of a power polymer as an adhesive component and other necessary ingredient thoroughly mixed together, granulating after once making the mixture into a slug, pressing a proper amount of such slug or granule with the use of a punch, die, or press, placing the constituents to form a nonadhesive layer thereon, and finally pressing the whole ingredients into a two-layer tablet. If the pressure applied in the second step of forming the nonadhesive layer on the adhesive layer is made higher than the pressure applied in the first step of forming the adhesive layer, the two layers are tightly bound together and will not hardly separate from each other, thus increasing the yield. The pressure for the respective steps may be determined appropricately.

The following examples illustrate the present invention in greater detail; however, it should be understood that the invention is in no way limited to these specific examples. These examples present experiments which were carried out to show the characteristic properties of the covering materials of the present invention as representative models.

EXAMPLE 1

This Example is to clarify the fact that a mixed preparation of the present invention consisting of cellulose lower alkyl ether and polyacrylic acid does not present a remarkable solubility, that it has excellent properties of swelling, retaining the form, and adhering to the mucous membrane, and that it is scarcely irritative to the mucous membrane.

(1-1): Finely powdered cellulose lower alkyl ether and polyacrylic acid of the present invention in amounts described in Table 1 were mixed thoroughly in the mixer and magnesium stearate corresponding to 0.5% of the total weight of the mixture was added thereto. The obtained homogeneous mixture was made into disks, each weighing approximately 90 mg, about 2 mm in thickness and 7 mm in diameter, having Monsanto hardness of about 5 to 10 kg.

The disks thus obtained were placed undisturbingly on an agar gel at 37° C. to observe the changes in the diameter and weight of the disks as an index of the swelling property and also to observe the changes in the form and the degrees of disintegration of the disks as an index of the form retainability. The results are shown in Table 1.

Also the same experiments were conducted with the disks prepared likewise from methyl cellulose, hydroxypropyl cellulose, and polyacrylic acid, each of which was used solely and from a 1:1 ratio mixture of polyacrylic acid and lactose. The results are also shown in Table 1.

disintegration of the disks were examined by obtaining the half-weight period according to the disintegration

TABLE 1

| | Constituent | | | | | | | | | | | | | | |
|---|---|---|---|---|---|---|---|---|---|---|---|---|---|---|---|
| | Methyl cellulose *3/ polyacrylic acid *2 | | | Hydroxyethyl cellulose *1/ polyacrylic acid *2 | | | Hydroxy- propylmethyl cellulose *5/ polyacrylic acid *2 | | | Hydroxypropyl cellulose/ polyacrylic acid | | | | | |
| Time for left standing (hrs) | Weight ratio | | | | | | | | | | | | | | |
| | 85/15 | | | 75/25 | | | 85/15 | | | 3/1 | | | 1/1 | | |
| | D *1 | W | F | D | W | F | D | W | F | D | W | F | D | W | F |
| 1 | 12.1 | — | Good | 14.0 | — | Good | 10.2 | — | Good | 12.2 | — | Good | 13.2 | — | Good |
| 3 | 18.8 | — | " | 21.0 | — | " | 15.1 | — | " | 19.0 | — | " | 27.6 | — | " |
| 6 | 23.6 | 98.0 | " | 30.5 | 162 | " | 21.6 | 89.2 | " | 25.2 | 91.5 | " | 35.3 | 93.1 | " |
| 10 | 30.8 | — | " | 37.2 | — | " | 30.2 | — | " | 31.4 | — | " | 37.2 | — | " |
| 22 | 40.2 | 183 | " | 48.0 | 241 | " | 38.1 | 172 | " | 42.9 | 190 | " | 47.9 | 195 | " |
| 52 | 63.3 | 283 | " | 61.2 | 358 | " | 55.3 | 296 | " | 60.2 | 265 | " | 56.1 | 254 | " |
| 76 | — | — | " | — | — | " | — | — | " | 70.3 | 281 | " | 59.0 | 292 | " |

| | Constituent | | | | | | | | | | | |
|---|---|---|---|---|---|---|---|---|---|---|---|---|
| Time for left Standing (hrs) | Hydroxypropyl cellulose | | | Methyl cellulose *3 | | | Polyacrylic acid *2 | | | Sodium polyacrylate *6/ lactose | | |
| | Weight ratio | | | | | | | | | | | |
| | | | | | | | | | | 50/50 | | |
| | D *1 | W | F | D | W | F | D | W | F | D | W | F |
| 1 | 9.4 | — | Partially dissolved | 10.2 | — | Partially dissolved | 39.6 | — | Good | 36.6 | — | Partially dissolved |
| 3 | 13.7 | — | Partially dissolved | 14.5 | — | Partially dissolved | 48.9 | — | " | 55.4 | — | Partially dissolved |
| 6 | 28.5 | — | Distinte-grated | 28.3 | — | Disinte-grated | 57.6 | 251 | " | 74.1 | — | Disinte-grated |
| 10 | — | — | Distinte-grated | — | — | Disinte-grated | 59.7 | — | " | — | — | Disinte-grated |
| 22 | — | — | Distinte-grated | — | — | Disinte-grated | 74.1 | — | " | — | — | Disinte-grated |
| 52 | — | — | Distinte-grated | — | — | Disinte-grated | 88.5 | 565 | " | — | — | Disinte-grated |
| 76 | — | — | Distinte-grated | — | — | Disinte-grated | 97.8 | 1006 | " | — | — | Disinte-grated |

*1–*6 in Table 1 mean as described below:
*1: D ... Increase in diameter (%), W ... Increase in weight (%), F ... Form retainability.
*2: Viscosity in a 0.2% aqueous solution (pH 7.3) at 25 ± 0.5° C. = 11.500 cpn
*3: Viscosity in a 2% aqueous solution at 20° C. = 1,335 cpn
*4: Viscosity in a 2% aqueous solution at 20° C. = 5,140 cpn
*5: Viscosity in a 2% aqueous solution at 20° C. = 143 cpn
*6: Degree of polymerization = 15,000–20,000

(1-2): Disks weighing about 40 mg, about 1 mm in thickness, 7 mm in diameter, and Monsanto hardness of 3 to 7 kg, were prepared from a mixture of cellulose lower alkyl ether and polyacrylic acid (weight ratio 85:15) according to the method of (1-1). The degrees of disintegration of the disks were examined by obtaining the half-weight period according to the disintegration test method provided in the Japanese pharmacopoeia, wherein the disks were fixed to a plastic plate and shaken in water. The results are shown in Table 2, from which it is apparent that the tablets of the present invention all have the excellent form retainability.

TABLE 2

| Cellulose ether | | Physical properties of tablets | | | Disintegrating property (Half-weight period) (min.) |
|---|---|---|---|---|---|
| Kinds | Viscosity (centi poise) *1 | Weight (mg) | Thickness (mm) | Hardness (kg) | |
| Methyl cellulose | 17.7 | 40.6 | 0.99 | 6.7 | 46 |
| | 28.9 | 42.2 | 1.00 | 6.6 | 46 |
| | 100 | 42.0 | 0.99 | 7.1 | 54 |
| | 382 | 39.7 | 0.99 | 6.9 | 55 |
| | 1,335 | 38.6 | 0.95 | 6.0 | 58 |
| | 4,160 | 42.6 | 1.02 | 7.1 | 52 |
| | 9,670 | 40.6 | 0.98 | 7.9 | 50 |
| Ethyl cellulose | 10.2 *2 | 40.7 | 1.28 | 6.4 | 40 |
| | 48.1 | 40.0 | 1.30 | 5.9 | 36 |
| | 100 | 40.3 | 1.33 | 4.9 | 54 |
| Hydroxyethyl cellulose | 320 | 40.3 | 1.00 | 4.1 | 35 |
| | 1,320 | 41.4 | 1.08 | 3.8 | 48 |
| | 5,140 | 40.1 | 0.97 | 4.3 | 48 |
| Hydroxypropyl cellulose | 3.5 | 39.3 | 1.08 | 5.3 | 22 |
| | 10.4 | 40.2 | 1.09 | 5.7 | 26 |
| | 61 | 41.3 | 1.12 | 5.9 | 52 |
| | 2,080 | 39.8 | 1.07 | 6.1 | 98 |
| Carboxymethyl | 615 | 42.0 | 0.86 | 7.3 | 13 |

TABLE 2-continued

| Kinds | Cellulose ether Viscosity (centi poise) *1 | Physical properties of tablets Weight (mg) | Thickness (mm) | Hardness (kg) | Disintegrating property (Half-weight period) (min.) |
|---|---|---|---|---|---|
| cellulose | | | | | |
| Sodium carboxy-methyl cellulose | 2,420 | 40.6 | 0.91 | 5.1 | 16 |
| Calcium carboxy-methyl cellulose | Swollen | 39.3 | 0.90 | 4.7 | 10 |
| Hydroxy propylmethyl cellulose | 9.5 | 38.9 | 0.97 | 5.5 | 25 |
| | 14.3 | 40.2 | 1.01 | 4.3 | 28 |
| | 19.3 | 39.0 | 1.02 | 4.2 | 29 |

*1: Measured in a 2% aqueous solution at 20° C.
*2: Measured in a 5% toluene-methanol solution at 25° C.

(1-3): In order to clarify the properties of the covering material of the present invention, the disks weighing 90 mg and measuring about 2 mm in thickness, 7 mm in diameter prepared according to the same method described in the foregoing (1-1) were experimented on the five subjects by adhering the disks to several parts in their oral cavities to observe the adhesion to the oral mucosa and the disintegration in the oral cavity. The results are shown in Table 3.

Also the same experiments were conducted with the disks, respectively comprising hydroxypropyl cellulose only, polyacrylic acid only, and a mixture of sodium polyacrylate and lactose in the ratio of 1:1, whose results are shown in Table 3.

a comparatively short time. Patches of white and even blisters were observed on the mucous membrane where they had been adhered. The disks consisting of polyacrylic acid and lactose swelled into an indefinite shape several times as large as the original one, thus breaking up thoroughly in a comparatively short time and making the mouth feel nasty on all sides. It was also confirmed that troches available on the market dissolved away in twenty minutes or so in the mouth.

(1-4): Disks weighing about 40 mg, measuring about 1.1 mm in thickness and 7 mm in diameter, and having Monsanto hardness of about 5 to 6 kg were also prepared. Their adhering property was inspected by adhering them to the mucous membrane inside the lower lips

TABLE 3

| | Constituent | | | | | | |
|---|---|---|---|---|---|---|---|
| | Hydroxypropyl cellulose + polyacrylic acid | | | | Hydroxypropyl cellulose | Polyacrylic acid | Polyacrylic acid + lactose |
| | Place of adhesion | | | | | | |
| Period (hrs) | Plate | Lip | Gum (outer surface) | Gum (outer surface) | Gum (outer surface) | Gum (outer surface) | Gum |
| 1 | | | | | | | |
| 2 | | | | | □ | □ | □ |
| 3 | ▨ | ▨ | ▨ | ▨ | | | |
| 4 | | | | | | | |
| 5 | | | | | | | |
| 6 | | | | | | | |
| : | | | | | | | |
| 18 | | | | | | | |
| 20 | | | | | | | |
| 22 | | | | | | | |

Remarks  ▨ mark denotes when a meal was taken    Disks dropped off during a meal.    Took two meals and sleep.

As mentioned in the above, the covering material of the present invention proves that it has excellent adhering and covering properties and outstanding resistance to disintegration and causes no inconvenience to speaking, smoking, eating, drinking, and sleeping wherever it may be applied, except for the lips which naturally make vigorous movements. Upon inspection made after the experiment was over, no abnormal state was found in the part where the disks had been adhered to the mucous membrane.

On the other hand, it was observed that the disks made of hydroxypropyl cellulose only showed a slightly weak adherence and also disintegrated to run down in a short time. The disks made of polyacrylic acid only, though proved themselves to have strong adherence, they somewhat lost strength after they swelled and started to disintegrate from their surfaces in of the five subjects. After they were left adhering to the mucous membrane for 4 hours, they were removed. 5 minutes and 30 minutes respectively after the removal of the disks, the surface of the mucous membrane where they had been adhered were inspected with the naked eye to study the irritability of the mucous membrane responding to the disks. The results are shown in Table 4.

The organic function test showed that the adhesion of the disks to the mucous membrane inside the lower lips of the five subjects was stronger when the content of the acrylic acid polymer was larger and that the disks were neither partially nor wholly stripped off during the 4-hour period of adhesion.

The same experiment was conducted on the disks comprising a mixture of hydroxypropyl cellulose and polyacrylic acid and similar results were obtained.

TABLE 4

| State of mucous membrane *1 | Subjects | Time of inspection | | | | | | | | | | | | | |
|---|---|---|---|---|---|---|---|---|---|---|---|---|---|---|
| | | After 5 minutes | | | | | | | After 30 minutes | | | | | | |
| | | constituent *2 | | | | | | | | | | | | | |
| | | 95/5 | 90/10 | 75/25 | 65/35 | 50/50 | 25/75 | 10/90 | 95/5 | 90/10 | 75/25 | 65/35 | 50/50 | 25/75 | 10/90 |
| Patches of white observed | A | − | − | − | − | − | + | ++ | − | − | − | − | − | + | + |
| | B | − | − | − | − | ± | + | + | − | − | − | − | − | ± | + |
| | C | − | − | − | − | ± | + | + | − | − | − | − | − | ± | ± |
| | D | − | − | ± | ± | ± | ++ | ++ | − | − | − | − | ± | + | + |
| | E | − | − | − | − | − | + | + | − | − | − | − | − | ± | ± |
| Minute blisters observed | A | − | − | − | − | − | + | + | − | − | − | − | − | ± | ± |
| | B | − | − | − | − | − | ± | + | − | − | − | − | − | ± | ± |
| | C | − | − | − | − | ± | ± | + | − | − | − | − | − | − | ± |
| | D | − | − | ± | ± | ± | + | + | − | − | − | − | − | ± | ± |
| | E | − | − | − | − | − | ± | ± | − | − | − | − | − | − | − |

*1: − none, ± almost none, + observed, ++ observed remarkably
*2: Methyl cellulose/polyacrylic acid (weight ratio)

Table 1, Table 2, and Table 3 show conclusively that the preparations having a mixed base of cellulose lower alkyl ether and polyacrylic acid of the present invention and the preparations having a single base of polyacrylic acid do not disintegrate, though continue to swell, even long after their administration, that they have an excellent form retainability keeping their form similar to the original one fairly well, without breaking up fast in water or in the wet oral cavity, and that they are good as covering material to be used by adhering to the injured part on the oral macosa. On the contrary, a single base consisting of cellulose lower alkyl ether and a mixed base consisting of sodium polyacrylate and lactose at the ratio of 1:1 started to partially dissolve immediately after their application, and disintegrated in a short time, thus proving themselves not fit for a base of a covering material to be used by adhering to the injured oral macosa. Also a single base consisting of cellulose lower alkyl ether is not good for practical use since it did not show enough adhesion to the mucous membrane and stripped off easily from the oral macosa in the application experiment. On the other hand, the organic function test conducted with a base consisting of cellulose lower alkyl ether and polyacrylic acid used in the present invention showed that the adhesion increased as the ratio of polyacrylic acid became higher. From the collective study of the results of Table 1, Table 2, and the abovementioned organic function test, a conclusion can be drawn to the effect that it is desirable to prepare a covering material to be used by adhering to the injured part on the oral mucosa from a mixture consisting of cellulose lower alkyl ether and polyacrylic acid (or its salt) with the higher mixing ratio of polyacrylic acid (or its salt). However, it should be noted that when the mixing ratio of polyacrylic acid in the mixture exceeds 50%, irritation caused to the oral macosa becomes strengthened, thus making its use as a covering material to be used by adhering to the injured part on the oral macosa improper.

The results shown in Table 1, Table 2, Table 3, and Table 4 make it apparent that a preparation consisting of about 50 to 99% by weight of cellulose lower alkyl ether and about 50 to 1% by weight of polyacrylic acid or its pharmaceutically acceptable salt is very suitable for a covering material to be used by adhering to the injured part on the oral mucosa.

EXPERIMENT 2

A covering material (30.0 mg per tablet) consisting of 85 parts of hydroxypropyl cellulose, 15 parts of polyacrylic acid, and 0.5 part of magnesium stearate. The preparation was administered to 10 patients suffering from recurrent stomatic aphtha on a prescription of 1 tablet at a time and 2 times per day to observe and judge three points including the degree of pain, size of the part affected by aphtha and the degree of flare. The judgement was formed in five grades, i.e. remarkably effective when aphtha and flare were completely cured in 1 to 4 days after the administration, effective when cured in 5 to 7 days, slightly effective when cured in 8 to 10 days, no change, and ingravescene.

The results were 3 cases of 'remarkably effective', 4 cases of 'effective', 3 cases of 'slightly effective', no case of 'no change', and no case of 'ingravescene' and the total of 'remarkably effective' and 'effective' cases makes an effective percentage of 70% and no ill effect was found with all the patients.

EXAMPLE 3

A homogeneous powder mixture for adhesive layer use was prepared by mixing 50 parts of polyacrylic acid polymer Carbopol 934 ®, 50 parts of hydroxypropyl cellulose, and 0.5 part of magnesium stearate as an adhesive layer base, aside from which a homogeneous powder mixture for nonadhesive layer use was also prepared by mixing 81 parts of lactose, 9 parts of hydroxypropyl cellulose, 10 parts of calcium carboxymethyl cellulose, and 0.5 part of magnesium stearate as a nonadhesive layer base.

Two-layer tablets were obtained having a diameter of about 7 mm, with a lower layer weighing about 40 mg and an upper layer weighing about 20 mg, from said adhesive layer powder as a material for the lower layer and said nonadhesive layer powder as a material for the upper layer, with the use of an ordinary multi-layer tablet machine.

EXAMPLE 4

The two-layer tablets described in Example 3 were tested with 30 pannelers to know how easily the tablets can be administered to the wet mucous membrane and how readily the tablets adhere (or move) to the opposite mucous membrane (gum). Each of the tablets was administered by placing it softly on the prescribed spot of the mucous membrane inside the lower lip with a pincette and by pressing it lightly to the prescribed spot on the anterior part of the palate with a clean finger tip. The results are shown in Table 5.

TABLE 5

|  | Number of failings Inside the lower lip | Number of tests Anterior part of palate | Adherence to the opposite membrane inside the lower lip |
|---|---|---|---|
| two layer tablet | 0/90 | 1/90 | 0/90 |

EXAMPLE 5

A two-layer covering material (55.0 mg per tablet) comprising an adhesive layer consisting of 85 parts of hydroxypropyl cellulose, 15 parts of polyacrylic acid and 0.5 parts of magnesium stearate and a supporting layer consisting of 90 parts of lactose, 7 parts of carboxymethyl cellulose calcium and 3 parts of hydroxypropyl cellulose was prepared. The preparation was administered to 89 patients suffering from recurrent stomatic aphtha on a prescription of 1 tablet at a time and 2 times per day and the results were observed and judged by doctors as to three points including the degree of pain, size of the part affected by aphtha, and the degree of flare. The judgement was formed in five grades, i.e. remarkably effective when aphtha and flare were completely cured in 1 to 4 days after the administration, effective when cured in 5 to 7 days, slightly effective when cured in 8 to 10 days, no change, and ingravescene.

The results were 45 cases of 'remarkably effective', 26 cases of 'effective', 13 cases of 'slightly effective', 4 cases of 'no change', and 1 case of 'ingravescence' and the total of 'remarkably effective' and 'effective' cases makes an effective percentage of 79.8% and no ill effect was found with all the patients.

What we claim is:

1. A method for treating an injured part on the oral mucosa, which comprises covering the injured part with a covering material consisting of a medicament-free adhesive layer consisting essentially of cellulose lower alkyl ether and polyacrylic acid or its pharmaceutically acceptable salt and a medicament-free nonadhesive layer which has no adhesion to the wet surface of the oral mucosa.

2. A method for treating an injured part on the oral mucosa according to claim 1, wherein the nonadhesive layer comprises water-soluble or water-disintegrable components.

3. A method for treating an injured part on the oral mucosa according to claim 2, wherein the nonadhesive layer comprises one or more than one kinds of components selected from the group consisting of lactose, glucose, sucrose, starch, crystalline cellulose, dextrin, cyclodextrin, silicic acid anhydride, talc, calcium stearate, magnesium stearate, bees wax, polyethylene glycol, polyphosphate, anhydrous calcium phosphate and carboxymethyl cellulose calcium.

* * * * *